United States Patent
Mack et al.

(10) Patent No.: US 10,881,663 B2
(45) Date of Patent: *Jan. 5, 2021

(54) METHOD OF TREATING PAIN IN ELDERLY PATIENTS WITH MILD RENAL IMPAIRMENT

(71) Applicant: Baudax Bio, Inc., Malvern, PA (US)

(72) Inventors: Randall J. Mack, Malvern, PA (US); Stewart McCallum, Malvern, PA (US); Alexis Gomez, Malvern, PA (US); Alex Freyer, Malvern, PA (US)

(73) Assignee: BAUDAX BIO, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,020

(22) Filed: Mar. 8, 2019

(65) Prior Publication Data

US 2019/0275053 A1     Sep. 12, 2019

Related U.S. Application Data

(60) Provisional application No. 62/749,407, filed on Oct. 23, 2018, provisional application No. 62/652,656, (Continued)

(51) Int. Cl.
*A61K 31/5415* (2006.01)
*A61P 29/00* (2006.01)
(Continued)

(52) U.S. Cl.
CPC ........ *A61K 31/5415* (2013.01); *A61K 9/0019* (2013.01); *A61K 9/10* (2013.01);
(Continued)

(58) Field of Classification Search
CPC .......... A61K 9/10; A61K 47/28; A61K 47/32; A61K 9/0019; A61K 31/5415; A61P 29/00
See application file for complete search history.

(56) References Cited

U.S. PATENT DOCUMENTS 10,463,673 B2   11/2019   Cooper et al.
2004/0229038 A1   11/2004   Cooper et al.
(Continued)

FOREIGN PATENT DOCUMENTS

EP     3090731 B1     11/2016

OTHER PUBLICATIONS

Aschoff (Opus National Capital Markets, Recro Pharma, Inc., Nov. 9, 2016; https://www.yournational.com/wp-content/uploads/2017/11/REPH-2016-11-09-initiation.pdf) (Year: 2016).*
(Continued)

*Primary Examiner* — Theodore R. Howell
(74) *Attorney, Agent, or Firm* — Troutman Pepper Hamilton Sanders LLP

(57) ABSTRACT

The present disclosure relates to administration of meloxicam intravenously, for treatment of pain, in patients who are at least 65 years old and have mild renal impairment, which can provide fast onset of pain relief suitable for management of acute pain as well as moderate to severe pain.

16 Claims, 2 Drawing Sheets

Related U.S. Application Data filed on Apr. 4, 2018, provisional application No. 62/640,232, filed on Mar. 8, 2018.

(51) Int. Cl.
| | | |
|---|---|---|
| *A61K 9/10* | (2006.01) | |
| *A61K 9/00* | (2006.01) | |
| *A61K 47/28* | (2006.01) | |
| *A61K 47/32* | (2006.01) | |
| *A61P 25/00* | (2006.01) | |

(52) U.S. Cl.
CPC .............. *A61K 47/28* (2013.01); *A61K 47/32* (2013.01); *A61P 29/00* (2018.01); *A61P 25/00* (2018.01)

(56) References Cited

U.S. PATENT DOCUMENTS

| | | |
|---|---|---|
| 2005/0288280 A1 | 12/2005 | Friton et al. |
| 2009/0004262 A1 | 1/2009 | Shaw et al. |
| 2010/0316725 A1 | 12/2010 | Ryde et al. |
| 2019/0275054 A1 | 9/2019 | Mack et al. |

OTHER PUBLICATIONS

Boulton-Jones et al. (Br J Clin Pharmacol, 1997, 43, 35-40). (Year: 1997).*
Schmid J, Busch U, Heinzel G, Bozler G, Kaschke S, Kummer M. Pharmacokinetics and metabolic pattern after intravenous infusion and oral administration to healthy subjects. Drug Metab Dispos. Nov. 1995;23(11):1206-13. PMID: 8591720. (Year: 1995).*
International Search Report and Written Opinion dated May 24, 2019 for International Application No. PCT/US2019/21354, 9 pages.
Gan, T. J. et al., "The Shortened Infusion Time of Intravenous Ibuprofen, Part 2: A Multicenter, Open-label, Surgical Surveillance Trial to Evaluate Safety," Clinical Therapeutics, 37(2):368-375 (2015).
Gottlieb, I. J. et al., "Evaluation of the safety and efficacy of an intravenous nanocrystal formulation of meloxicam in the management of moderate-to-severe pain after bunionectomy," Journal of Pain Research, 11:383-393 (2018).
International Search Report and Written Opinion dated Jan. 10, 2020 for International Application No. PCT/US2019/060278.
FDA Formula N1539, Jul. 26, 2017.
"Recro Pharma Initiates Pivotal Phase III Clinical Trial of IV Meloxicam for Acute Postoperative Pain," Recro Pharma, Jan. 27, 2016, 2 pages.
"Recro Pharma Presents Clinical Data at PAINWeek 2016: Poster Highlights Efficacy and Safety of IV Meloxicam in Subjects with Moderate to Severe Pain Following Bunionectomy," MarketWatch, Sep. 7, 2016, 4 pages.

* cited by examiner

METHOD OF TREATING PAIN IN ELDERLY PATIENTS WITH MILD RENAL IMPAIRMENT

CROSS REFERENCE TO RELATED APPLICATIONS

This application claims the benefit under 35 U.S.C. § 119(e) of U.S. Provisional Patent Application No. 62/640,232, filed Mar. 8, 2018, U.S. Provisional Patent Application No. 62/652,656, filed Apr. 4, 2018, and U.S. Provisional Patent Application No. 62/749,407, filed Oct. 23, 2018. The contents of these applications are incorporated herein by reference in their entireties for all purposes.

FIELD OF THE DISCLOSURE

The present disclosure relates to methods of administering meloxicam for treatment of pain, including intravenous administration, in elderly patients with mild renal impairment.

BACKGROUND OF THE DISCLOSURE

Meloxicam (4-hydroxy-2-methyl-N-(5-methyl-2-thiazolyl)-2H-1,2-benzothiazine-3-carboxamide-1,1-dioxide) is a long-acting non-steroidal-anti-inflammatory drug (NSAID) that possesses anti-inflammatory, analgesic, and antipyretic activities, which are believed to be related to the inhibition of cyclooxygenase (COX) and subsequent reduction in prostaglandin biosynthesis. Meloxicam has been marketed by Boehringer Ingelheim Pharmaceuticals, Inc. since the 1990's as an oral agent, Mobic®. Mobic is used for treatment of symptoms of osteoarthritis and rheumatoid arthritis.

Oral meloxicam, however, has a slow onset of action, largely due to poor water solubility. The oral form has a prolonged absorption time, with the time of maximum observed plasma concentration ($t_{max}$) being approximately 5-7 hours following oral administration, which is consistent with its poor water solubility. As such, oral meloxicam is not used for the treatment of acute pain.

Intravenous (IV) administration of the NSAID ibuprofen was approved in 2009 for pain management; however, an infusion time of 30 minutes is required and it must be administered every 6 hours. See CALDOLOR® Prescribing Information. Further, patients receiving IV administration of NSAIDs report high rates of injection site pain or discomfort (e.g., 16%-24% reported), which prohibits faster administration times. See Bergese, S. G., et al., *Clinical Therapeutics*, 2015, 37, 368-375. Therefore, current approved IV NSAID formulations have significant drawbacks.

Additionally, the use of NSAID for the treatment of pain may be complicated by the metabolic variations among patients. More specifically, age, impaired liver function, and impaired kidney function can each alter a patient's ability to metabolize an NSAID. For example, in order to safely treat elderly patients or patients with impaired liver or kidney function (e.g., patients with mild, moderate, or severe renal impairment), dose adjustment are commonly required, because normal doses of the NSAID (i.e., the dose the patient would otherwise be administered based on the current FDA approved label) may present an unacceptable risk to the patient. The proper dose for patients with one or more of the above characteristics is unpredictable. For example, such patients may require a reduced dose (i.e., reduced relative to the normal dose); however, the reduced dose may not provide the patient with appropriate plasma levels of the NSAID needed to properly treat pain. The situations is worse for patients that have combination of said metabolic factors, such as elderly patients with impaired kidney function (e.g., elderly patients with mild renal impairment). Indeed, a substantial number of elderly patients with impaired kidney function undergo surgical procedures and require treatment for surgical pain.

Thus, there is a need for a method of administering meloxicam which can provide a faster onset of action, a longer therapeutic window, without the need for multiple injections a day. Such methods would be advantageous in providing rapid treatment for pain, including acute and mild to moderate or moderate to severe pain. More specifically, there is a need to establish safe and efficacious treatment of pain in subpopulation of elderly patient with renal impairment who may have increased risk of complications and toxicities with NSAID use.

SUMMARY OF THE DISCLOSURE

Among other things, the present invention is directed to a method of treating pain in a patient in need thereof, comprising administering meloxicam to the patient intravenously at a dose in the range of from about 5 mg to about 200 mg, wherein the patient is at least 65 years old and has mild renal impairment.

In one embodiment of the method as disclosed herein, the meloxicam is in a form of meloxicam nanocrystals.

In one embodiment of the method as disclosed herein, the dose of meloxicam is administered to the patient as a bolus dose.

In one embodiment of the method as disclosed herein, the dose of meloxicam is administered to the patient over the course of about 1 to about 60 seconds. In another embodiment, the dose of meloxicam is administered to the patient over the course of about 5 to about 45 seconds. In other embodiments, the bolus dose of meloxicam is administered to the patient over the course of about 15 to about 30 seconds.

In one embodiment of the method as disclosed herein, the dose of meloxicam is in the range of from about 15 mg to about 180 mg. In some embodiments, the dose of meloxicam is about 30 mg.

In one embodiment of the method as disclosed herein, the dose of meloxicam is present in a volume of from about 0.5 mL to about 4 mL. In another embodiment, the dose of meloxicam is present in a volume of about 1 mL.

In one embodiment of the method as disclosed herein, the pain treated is post-surgical pain.

In one embodiment of the method as disclosed herein, the dose of meloxicam is administered after the patient has undergone a surgical procedure. In one embodiment, the surgical procedure is an open surgical procedure. In another embodiment, the surgical procedure is a laparoscopic surgical procedure. In other embodiments, the surgical procedure was performed on hard tissue. In some embodiments, the surgical procedure was performed on soft tissue.

In one embodiment of the method as disclosed herein, the pain treated is moderate to severe pain. In another embodiment, the pain treated is mild to moderate pain.

DETAILED DESCRIPTIONS OF THE DISCLOSURE

Figure 1:
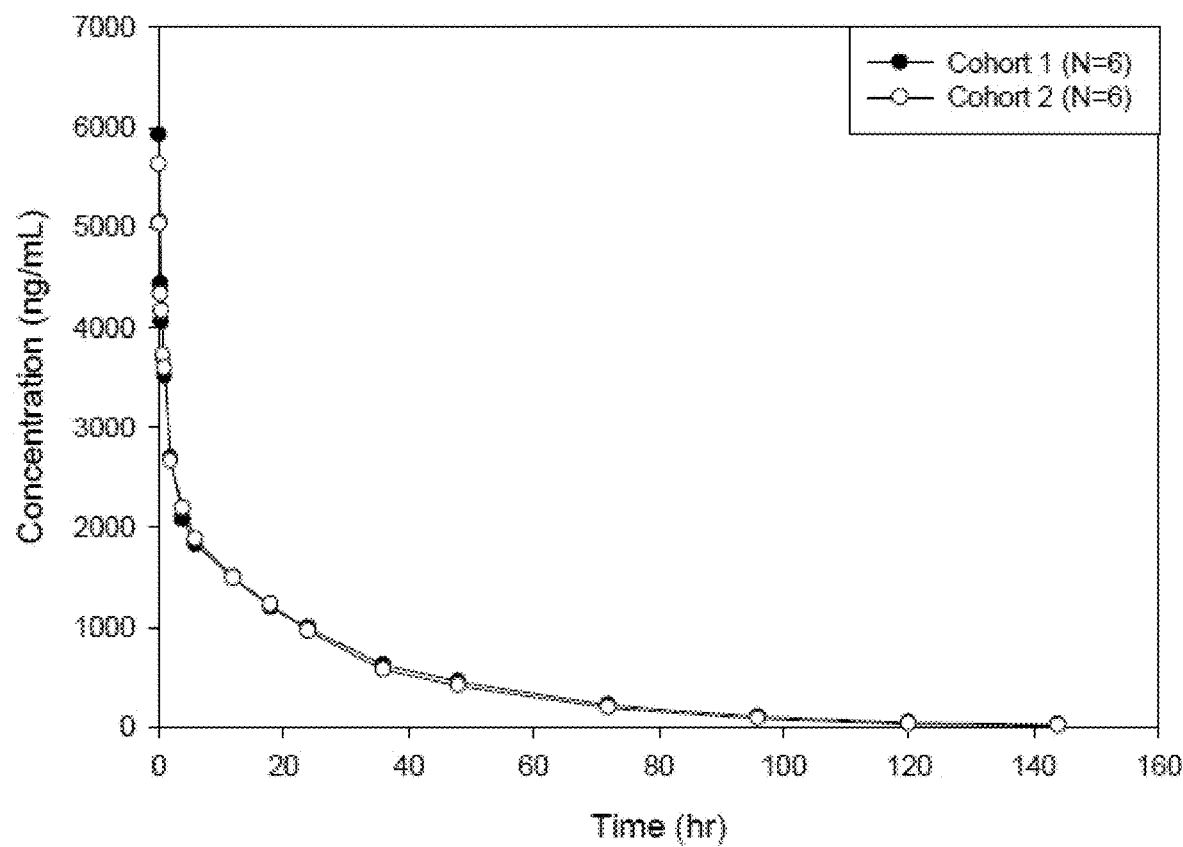
FIG. 1 shows mean meloxicam plasma concentrations over time in linear scale in subjects studied in Example 3.

The present disclosure relates to methods of treating pain in a patient in need thereof with meloxicam. In one embodiment, the meloxicam is administered to a patient who is at least 65 years old and has renal impairment. In other embodiments, the meloxicam is administered to a patient who is at least 65 years old and has mild renal impairment. In another embodiment, the meloxicam is administered to a patient intravenously. In another embodiment, the meloxicam is administered to a patient intravenously in a bolus dose In some embodiments, the meloxicam is administered to a patient intravenously in a bolus dose of about 30 mg.

Definitions

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein in references to a measurable value such as an amount of weight, time, dose, etc. is meant to encompass values within an acceptable degree of variability in the art. In some embodiments, degree of variability is based on FDA guidelines.

As used herein, "meloxicam" refers to 4-hydroxy-2-methyl-N-(5-methyl-2-thiazolyl)-2H-1,2-benzothiazine-3-carboxamide-1,1-dioxide, which has the structure as depicted below. The molecular weight is 351.4. Its molecular formula is $C_{14}H_{13}N_3O_4S_2$.

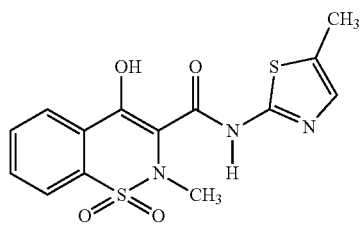 [SMILES: Cc1cnc(NC(=O)C2=C(O)c3ccccc3S(=O)(=O)N2C)s1]

As used herein, the term "bolus dose" refers to a discrete amount of a medication or a drug, e.g., meloxicam, which is given within a specific time. The specific time over which the bolus dose is administered (also referred to herein as the infusion rate) may be any suitable time which provides rapid onset of action (i.e., pain relief) and which does not cause significant injection site pain, such as a significant burning sensation. In some embodiments, the infusion time may be about 1 minute or less.

As used herein, the term "normal renal function" refers to a human subject with a glomerular filtration rate (GFR) greater than or equal to 90 mL/min/1.73 m$^2$ (or 90 mL/min) or an estimated glomerular filtration rate (eGFR) greater than or equal to 90 mL/min (or 90 mL/min/1.73 m$^2$).

As used herein, the term "mild renal function" refers to a human subject with a glomerular filtration rate (GFR) from 60 mL/min/1.73 m$^2$ to 89 mL/min/1.73 m$^2$ (or from 60 mL/min to 89 mL/min) or an estimated glomerular filtration rate (eGFR) from 60 mL/min to 89 mL/min (or from 60 mL/min/1.73 m$^2$ to 89 mL/min/1.73 m$^2$).

As used herein, the term "moderate renal function" refers to a human subject with a glomerular filtration rate (GFR) from 30 mL/min/1.73 m$^2$ to 59 mL/min/1.73 m$^2$ (or from 30 mL/min to 59 mL/min) or an estimated glomerular filtration rate (eGFR) from 30 mL/min to 59 mL/min (or from 30 mL/min/1.73 m$^2$ to 59 mL/min/1.73 m$^2$).

As used herein, the term "sever renal function" refers to a human subject with a glomerular filtration rate (GFR) from 15 mL/min/1.73 m$^2$ to 29 mL/min/1.73 m$^2$ (or from 15 mL/min to 29 mL/min) or an estimated glomerular filtration rate (eGFR) from 15 mL/min to 29 mL/min (or from 15 mL/min/1.73 m$^2$ to 29 mL/min/1.73 m$^2$).

As used herein the term "$AUC_{inf}$" or "$AUC_{0-\infty}$" refers to area under the plasma concentration time curve from time zero to infinity or time zero to time of last quantifiable concentration.

Therapeutic Use

While oral administration of meloxicam is approved for treating inflammation (e.g., osteoarthritis and rheumatoid arthritis), currently available oral formulations of meloxicam are known to have a slow onset of action due to poor solubility of meloxicam. The slow onset of action of oral meloxicam has rendered meloxicam not appropriate for acute pain management (e.g., mild to moderate pain and/or moderate to severe pain).

The inventors discovered that an intravenous formulation of meloxicam may be administered to provide a rapid onset of action of meloxicam that is critical for treatment of acute pain. Meloxicam nanocrystals significantly improves the solubility of the meloxicam, allowing for higher concentrations of meloxicam to be administered intravenously compared to an otherwise similar formulation in which meloxicam is not prepared as nanocrystals. Specifically, the inventors found that a meloxicam dose of about 5 mg to about 200 mg can provide a rapid onset of action of meloxicam while being efficacious and safe for the treatment of acute pain (e.g., mild to moderate pain and/or moderate to severe pain). In contrast to other intravenous NSAIDs such as ibuprofen and acetaminophen, meloxicam nanocrystals can be safely administered intravenously without causing injection site pain. In addition, the inventors found that a bolus dose given over of about 60 seconds (e.g., about 1 to about 60 seconds, about 1 to 30 seconds, about 15 to about 30 seconds, etc.) was safe and effective for the treatment of pain.

In one embodiment, the methods disclosed herein comprise administering to the patient a dose of meloxicam intravenously, wherein the meloxicam is at a dose of about 30 mg. In some embodiments, the methods disclosed herein comprise administering to the patient a dose of meloxicam intravenously, wherein the meloxicam is at a concentration of about 30 mg/mL. In one embodiment, the intravenous dose is a bolus dose.

Drug doses are commonly adjusted for patients with renal impairment according to creatinine clearance or glomerular filtration rate as an inappropriate dose (or often dose appropriate for patients with normal renal function) in patients with renal impairment. However, such adjustment can be result in a treatment that is either ineffective or causes toxicity.

Further, the inventors discovered that the same dose of meloxicam was safe and efficacious for the subpopulation of patients who are at least 65 years old with mild renal impairment when compared to subject with normal renal impairment. More specifically, the subpopulation of patients who are at least 65 years old with mild renal impairment did not show any clinically significant differences in pharmacokinetic parameters when compared to subject with normal renal function. This was surprising as both age and renal impairment are well-known in the art to decrease the rate of drug clearance from the body, and such patients are commonly treated with a reduced dose of a drug. The findings are even more surprising because intravenous meloxicam is contraindicated in patients with moderate and sever renal impairment.

In one embodiment, the meloxicam is in a form of meloxicam nanocrystals. In another embodiment, meloxicam nanocrystals are formed using Alkermes NanoCrystal™ technology. See U.S. Pat. No. 8,512,727 which is hereby incorporated by reference in its entirety for all purposes.

In one embodiment of the method as disclosed herein, the IV dose (including a bolus dose) of meloxicam is administered to the patient over the course of about 1 to about 60 seconds, including all values and subranges therebetween. That is, the IV dose of meloxicam may be administered to patient in about 1 second, about 2 seconds, about 3 seconds, about 4 seconds, about 5 second, about 6 seconds, about 7 seconds, about 8 seconds, about 9 second, about 10 seconds, about 11 second, about 12 seconds, about 13 seconds, about 14 seconds, about 15 second, about 16 seconds, about 17 seconds, about 18 seconds, about 19 second, about 20 seconds, about 21 second, about 22 seconds, about 23 seconds, about 24 seconds, about 25 second, about 26 seconds, about 27 seconds, about 28 seconds, about 29 second, about 30 seconds, about 31 second, about 32 seconds, about 33 seconds, about 34 seconds, about 35 second, about 36 seconds, about 37 seconds, about 38 seconds, about 39 second, about 40 seconds, about 41 second, about 42 seconds, about 43 seconds, about 44 seconds, about 45 second, about 46 seconds, about 47 seconds, about 48 seconds, about 49 second, about 50 seconds, about 51 second, about 52 seconds, about 53 seconds, about 54 seconds, about 55 second, about 56 seconds, about 57 seconds, about 58 seconds, about 59 second, or about 60 seconds, or any ranges between these values.

For example, in some embodiments, the IV dose (including a bolus dose) of meloxicam is administered to the patient over the course of about 5 to about 45 seconds. In other embodiments, the IV dose of meloxicam is administered to the patient over the course of about 10 to about 40 seconds. In still other embodiments, the IV dose of meloxicam is administered to the patient over the course of about 15 to about 35 seconds. In some embodiments, the IV dose of meloxicam is administered to the patient over the course of about 10 to about 30 seconds. In certain embodiments, the IV dose of meloxicam is administered to the patient over the course of about 15 to about 30 seconds. In one embodiment, the IV dose of meloxicam is administered to the patient over about 15 seconds.

The infusion rates of the present disclosure are significantly quicker than the FDA-approved infusion time of CALDOLOR® (an intravenous formulation of the NSAID ibuprofen), which requires at least 30 minutes. See CALDOLOR® Prescribing Information. Similarly, the infusion rates of the present disclosure are also significantly faster than infusion rates for OFIRMEV® (an intravenous formulation of acetaminophen), which requires a 15 minute infusion rate. See OFIRMEV® Prescribing Information. Whereas intravenous formulations of ibuprofen and acetaminophen cause injection site pain when administered at a rate that is faster than 15 minutes and 30 minutes, respectively, the present formulations were surprisingly discovered not to cause such injection site pain when administered in a IV dose (including a bolus dose).

Further, the inventors discovered that an injection of meloxicam within seconds, according to the methods disclosed herein, achieves fast onset of analgesics which is critical for management of acute pain, such as post-surgical pain. For example, in one embodiment, the dose of meloxicam administered intravenously to a patient can provide pain relief within about 10 minutes. This rapid onset of pain relief provided by the methods of the present disclosure is a substantial improvement from available intravenous NSAIDs, such as ketorolac which can take up to 30 minutes for the onset of pain relief. See Ketorolac Tromethamine Injection Prescribing Information.

Moreover, unlike the previously reported NSAID injections which resulted in high injection site pain adverse effects (e.g., 16%-24% reported), the inventors found that the injection methods for administration of meloxicam disclosed herein is safe and efficacious, as only 2% of patients receiving a dose of intravenous meloxicam reported injection site pain.

In one embodiment of the methods disclosed herein, the dose of meloxicam is in the range of from about 1 mg to about 250 mg, inclusive of all values and subranges therebetween. That is, the dose of meloxicam may be about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, 215 mg, about 220 mg, 225 mg, about 230 mg, 235 mg, about 240 mg, 245 mg, or about 250 mg, or any ranges between these values.

In one embodiment, the dose of meloxicam is in the range of from about 5 mg to about 200 mg. In some embodiments, the dose of meloxicam is in the range of from about 15 mg to about 180 mg. In some embodiments, the dose of meloxicam is in the range of from about 15 mg to about 100 mg. In other embodiments, the dose of meloxicam is in the range of from about 15 mg to about 80 mg. In some embodiments, the dose of meloxicam is in the range of from about 20 mg to about 70 mg. In some embodiments, the dose of meloxicam is in the range of from about 30 mg to about 60 mg. In some embodiments, the dose of meloxicam is about 30 mg. In another embodiment, the dose of meloxicam is about 60 mg.

In some embodiments, the intravenous meloxicam is formulated at a concentration of from about 10 mg/mL to about 50 mg/mL, e.g., about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, and about 60 mg/mL, inclusive of all values and subranges therebetween. In particular embodiments, the intravenous meloxicam is formulated at a concentration of about 30 mg/mL.

In one embodiment, the dose of meloxicam as disclosed herein is administered once a day, twice a day, three times a day, every other day, or at a frequency deemed appropriate by a physician. In one embodiment, the dose of meloxicam is administered once a day intravenously. In some embodiments, meloxicam is administered about every 16-26 hours (e.g., about 16, about 17, about 18, about 19, about 20, about 21, about 22, about 23, about 24, about 25, or 26 hours, inclusive of all values and subranges therebetween) until the patient is no longer in need thereof. As used herein, a "patient is no longer in need thereof" when the pain has subsided or the patient is discharged from the hospital. In some embodiments, meloxicam is administered intravenously about once every 6 hours, about once every 8 hours, about once every 12 hours, about once every 18 hours, about once every 24 hours, about once every 36 hours, about once every 48 hours or at a frequency deemed appropriate by a physician. In particular embodiments, meloxicam is administered once every 18-24 hours.

In some embodiments, the methods comprise administering meloxicam to a subject at about 18 hours, at about 24 hours, at about 36 hours, at about 48 hours, at about 54 hours, at about 72 hours, at about 96 hours, at about 5 days, at about 6 days, and so forth subsequent to the first dose of meloxicam administered to the subject.

In one embodiment, the dose of meloxicam as disclosed herein can be administered to a subject about every 16 hours to about every 26 hours (e.g., about every 18-24 hours) for 1 day, 2 days, 3 days, 4 days, 5 days, 6 days, 7 days, 8 days, 9 days, 10 days, 11 days, 12 days, 13 days, 14 days, or at a duration and frequency deemed appropriate by a physician.

In one embodiment, a single dose, including a bolus dose, as disclosed herein can provide a rapid treatment which lasts for about 12 hours to about 48 hours. In one embodiment, a single dose as disclosed herein can provide a rapid treatment which lasts for about 24 hours. The ability for the presently disclosed meloxicam formulation to provide treatment lasting about 24 hours is a significant improvement over previously approved NSAID IV treatments, such as CALDOLOR® which requires infusion every 6 hours. See CALDOLOR® Prescribing Information.

In any of the methods disclosed herein, meloxicam can be administered for treatment of pain or for pain management. In one embodiment, meloxicam can be administered for the treatment or management of acute pain. In one embodiment, meloxicam can be administered for the treatment or management of moderate to severe pain. In one embodiment, meloxicam can be administered for the treatment or management of acute moderate to severe pain. In one embodiment, meloxicam can be administered for the treatment or management of mild to moderate pain. In one embodiment, meloxicam can be administered for the treatment or management of acute mild to moderate pain. In one embodiment, the pain management is for a human patient. In one embodiment, the human patient is an adult (e.g., aged 17 or older).

In one embodiment of the method as disclosed herein, the pain treated is post-surgical pain. Post-surgical pain may include two clinically important aspects, namely resting pain, or pain that occurs when the patient is not moving, and mechanical pain which is exacerbated by movement (coughing/sneezing, getting out of bed, physiotherapy, etc.). In some embodiments, resting pain is treated, in some embodiments, mechanically-induced pain (including pain resulting from movement) is treated, and in some embodiments, thermally-induced pain is treated. In some embodiments, allodynia (i.e., increased response (i.e., increased noxious sensation) to a normally non-noxious stimulus) is treated. In some embodiments, hyperalgesia (i.e., increased response to a normally noxious or unpleasant stimulus) is treated. In some embodiments, allodynia and/or hyperalgesia is thermal or mechanical (tactile) in nature, or resting pain. In some embodiments, the pain is associated with site of incision, wound or trauma, and/or proximal, at or near the site of incision, wound, and/or trauma. In some embodiments, the pain is nociceptive pain, including superficial somatic pain, deep somatic pain and visceral pain; in some embodiments, the pain is neuropathic pain such as central neuropathic pain and peripheral neuropathic pain.

In some embodiments, the surgical procedure is performed on hard and/or soft tissue. In some embodiments, the surgical procedure is performed on soft tissue. In some embodiments, the soft tissue surgery may include, but is not limited to, reproductive surgery, abdominal surgery, thoracic surgery, upper airway surgery, head and neck surgery, neurosurgery, surgical oncology and wound care and reconstruction. In some embodiments, soft tissues include, but are not limited to, tendons, ligaments, fascia, skin, fibrous tissues, fat, and synovial membranes (which are connective tissue), and muscles, nerves and blood vessels (which are not connective tissue). In other embodiments, the surgical procedure is performed on hard tissue. Hard or calcified tissues include tissues which are mineralized and have a firm intercellular matric. Non limiting examples of hard tissues are bone, tooth enamel, dentin, and cementum.

In some aspects, the surgery is open surgery, which refers to a procedure involving cutting of skin and tissues so that a surgeon has a full view of the structures or organs involved. Non-limiting examples of open surgery include removal of organs, such as gall bladder or kidneys, organ transplant, removal of a brain tumor, removal of a damaged kidney or open-heart surgery.

In some aspects, the surgery is a minimally invasive surgery, which refers to a procedure that typically does not involve generating a large incision. Non-limiting examples of minimally invasive surgery include laparoscopy, endoscopy, arthroscopy, bronchoscopy, cystoscopy, gastroscopy, hysteroscopy, laryngoscopy and sigmoidoscopy. In some embodiments, the surgical procedure is a laparoscopic surgical procedure. Typically, laparoscopy is a surgical procedure involving generating small incisions (cuts) in the wall of the abdomen and inserting a laparoscope (a thin, lighted tube) into one of the incisions. In some embodiments, during laparoscopy, other instruments may be inserted through the same or other incisions to perform procedures such as removing organs or taking tissue samples to be checked under a microscope for signs of disease. Non-limiting examples of laparoscopic procedures are gynecological surgery, lymphadenectomy, kidney surgery, radical prostatectomy, livery surgery, gallbladder removal (cholecystectomy), appendectomy, hernia repair, removal of part of the colon (colectomy) or small intestine, surgery for acid-reflux disease (fundoplication), removal of adrenal glands, and removal of the spleen. In some aspects, the surgery may be microsurgery, which typically is used for delicate work on very small body structures relying on special equipment and microscopes to magnify the area to be operated on and using tiny surgical instruments. Non-limiting examples of microsurgeries are vasectomy reversal or re-attaching a severed finger. In some embodiments, the surgery is robotic-assisted surgery, in which a surgeon maneuvers robotic arms during the procedure allowing for more precise movements. Non-limiting examples of robotic surgery include surgeries on the head and neck, gynecologic and urologic surgeries like hysterectomies and prostate cancer treatments.

In some embodiments, the surgery is colorectal surgery, while in other embodiments, the surgery is orthopedic surgery. In some embodiments, the surgery is joint replacement surgery. In some embodiments, the surgery is unilateral total knee arthroplasty.

In one embodiment of the method as disclosed herein, the dose of meloxicam is administered after the patient has undergone a surgical procedure. In one embodiment, the surgical procedure is an open surgical procedure. In another embodiment, the surgical procedure is a laparoscopic surgical procedure. In other embodiments, the surgical procedure was performed on hard tissue. In some embodiments, the surgical procedure was performed on soft tissue.

Formulations

In one embodiment, the dose for an IV injection or an IV infusion disclosed herein can comprise one or more pharmaceutically acceptable excipients or carriers known to one skilled in the art.

In one embodiment, a pharmaceutically acceptable excipient for the dose for an IV injection or an IV infusion can include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, sodium deoxycholate (deoxycholic acid), starch tragacanth, sucrose or xanthan gum.

In one embodiment, the dose of meloxicam disclosed herein for injection or infusion can be formulated in liquid carriers such as, but not limited to, water, dextrose in water, glucose in water, vegetable oil, alcohol, polyethylene glycol, propylene glycol, or glycerin. In one embodiment, the dose of meloxicam disclosed herein for injection is formulated in sterile water.

In one embodiment, the dose of meloxicam is in a form of aqueous dispersion.

In one embodiment of the method as disclosed herein, the dose of meloxicam is present in a volume of from about 0.5 mL to about 4 mL, inclusive of all values and subranges therebetween. That is, the IV dose (including a bolus dose) of meloxicam is present in a volume of about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, about 1.6 mL, about 1.7 mL, about 1.8 mL, about 1.9 mL, about 2.0 mL, about 2.1 mL, about 2.2 mL, about 2.3 mL, about 2.4 mL, about 2.5 mL, about 2.6 mL, about 2.7 mL, about 2.8 mL, about 2.9 mL, about 3.0 mL, about 3.1 mL, about 3.2 mL, about 3.3 mL, about 3.4 mL, about 3.5 mL, about 3.6 mL, about 3.7 mL, about 3.8 mL, about 3.9 mL, or about 4.0 mL, or any ranges between these values. In another embodiment, the dose of meloxicam is present in a volume of about 1 mL.

In one embodiment of the method as disclosed herein, the dose of meloxicam is present at a concentration of about 30 mg/mL. That is, the dose of meloxicam can be present at a concentration between 28.5 mg/mL and 31.5 mg/mL or any subranges between the two values. In some embodiments, the dose of meloxicam can be present at a concentration of about 10 mg/mL to about 40 mg/mL, such as, for example, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, and about 40 mg/mL inclusive of all values and subranges therebetween. In one embodiment, the dose of meloxicam as disclosed herein can be a bolus dose.

In one embodiment, the dose of meloxicam is present at a concentration of about 30 mg/mL as a single use vial.

As previously noted, meloxicam has poor water solubility, which is one of the main reasons oral administration is not suitable for treatment of acute pain. Further, due to meloxicam's poor water solubility, it is challenging to provide an injectable formulation that is sufficiently concentrated so that the formulation can be injected to patients in seconds in order to achieve rapid onset of pain relief without causing injection site pain. However, the inventors were able to increase the meloxicam concentration to 30 mg/mL. This is a 20% increase in the concentration of meloxicam as compared to an otherwise similar formulation in which meloxicam is not prepared as nanocrystals, which is substantial considering meloxicam is poorly water soluble. The concentration of meloxicam as disclosed herein is critical to providing an IV dose and achieving rapid onset of pain relief without causing injection site pain. At concentrations of meloxicam which are higher than those disclosed herein, the drugs can crystalize out of solution, which will interfere with the injectability and/or syringeability of the formulation. At concentrations of meloxicam which are lower than those disclosed herein, the larger volumes of carrier preclude administration within the time ranges specified herein, and thereby cannot achieve rapid onset of pain relief.

In one embodiment, the dose of meloxicam as disclosed herein is used with dilution. In one embodiment, the dose of meloxicam as disclosed herein is used without dilution. In one embodiment, the 30 mg/mL dose of meloxicam is used without dilution. In one embodiment, the 30 mg/mL dose of meloxicam is not added to an IV solution or an IV fluid bag. That is, the 30 mg/mL dose of meloxicam as disclosed herein is administered to a patient in need thereof as 30 mg/mL.

Pharmacokinetics

In one embodiment, a 1 mL bolus of 30 mg IV dose of meloxicam provides an average blood plasma $C_{max}$ of meloxicam within about 80% to about 125% of the range of from about 4000 ng/mL to about 11000 ng/mL in a patient who is at least 65 year old with mild renal impairment, inclusive of all values and subranges therebetween. That is, a 1 mL bolus of a 30 mg IV dose of meloxicam can provide plasma $C_{max}$ of about 3000 ng/mL, about 3100 ng/mL, about 3200 ng/mL, about 3300 ng/mL, about 3400 ng/mL, about 3500 ng/mL, about 3600 ng/mL, about 3700 ng/mL, about 3800 ng/mL, about 3900 ng/mL, about 4000 ng/mL, about 4100 ng/mL, about 4200 ng/mL, about 4300 ng/mL, about 4400 ng/mL, about 4500 ng/mL, about 4600 ng/mL, about 4700 ng/mL, about 4800 ng/mL, about 4900 ng/mL, about 5000 ng/mL, about 5100 ng/mL, about 5200 ng/mL, about 5300 ng/mL, about 5400 ng/mL, about 5500 ng/mL, about 5600 ng/mL, about 5700 ng/mL, about 5800 ng/mL, about 5900 ng/mL, about 6000 ng/mL, about 6100 ng/mL, about 6200 ng/mL, about 6300 ng/mL, about 6400 ng/mL, about 6500 ng/mL, about 6600 ng/mL, about 6700 ng/mL, about 6800 ng/mL, about 6900 ng/mL, about 7000 ng/mL, about 7100 ng/mL, about 7200 ng/mL, about 7300 ng/mL, about 7400 ng/mL, about 7500 ng/mL, about 7600 ng/mL, about 7700 ng/mL, about 7800 ng/mL, about 7900 ng/mL, about 8000 ng/mL, about 8100 ng/mL, about 8200 ng/mL, about 8300 ng/mL, about 8400 ng/mL, about 8500 ng/mL, about 8600 ng/mL, about 8700 ng/mL, about 8800 ng/mL, about 8900 ng/mL, about 9000 ng/mL, about 9100 ng/mL, about 9200 ng/mL, about 9300 ng/mL, about 9400 ng/mL, about 9500 ng/mL, about 9600 ng/mL, about 9700 ng/mL, about 9800 ng/mL, about 9900 ng/mL, about 10000 ng/mL, about 10100 ng/mL, about 10200 ng/mL, about 10300 ng/mL, about 10400 ng/mL, about 10500 ng/mL, about 10600 ng/mL, about 10700 ng/mL, about 10800 ng/mL, about 10900 ng/mL, about 11000 ng/mL, about 11100 ng/mL, about 11200 ng/mL, about 11300 ng/mL, about 11400 ng/mL, about 11500 ng/mL, about 11600 ng/mL, about 11700 ng/mL, about 11800 ng/mL, about 11900 ng/mL, about 12000 ng/mL, about 12100 ng/mL, about 12200 ng/mL, about 12300 ng/mL, about 12400 ng/mL, about 12500 ng/mL, about 12600 ng/mL, about 12700 ng/mL, about 12800 ng/mL, about 12900 ng/mL, about 13000 ng/mL, about 13100 ng/mL, about 13200 ng/mL, about 13300 ng/mL, about 13400 ng/mL, and about 13500 ng/mL, or any values or ranges between above values, in a patient who is at least 65 year old with mild renal impairment.

In one embodiment, a 1 mL bolus of a 30 mg IV dose of meloxicam provides an average blood plasma $C_{max}$ within about 80% to about 125% of the range of from about 4500 ng/mL to about 7500 ng/mL in a patient who is at least 65 year old with mild renal impairment, inclusive of all values and subranges therebetween. In one embodiment, a 1 mL bolus of a 30 mg IV dose of meloxicam provides an average plasma $C_{max}$ within the range of from about 80% to about 125% of 5920±842 ng/mL in a patient who is at least 65 year old with mild renal impairment, inclusive of all values and subranges therebetween. In one embodiment, a 1 mL bolus of a 30 mg IV dose of meloxicam provides an average plasma $C_{max}$ within the range of from about 4062 ng/mL to about 8453 ng/mL in a patient who is at least 65 year old with mild renal impairment, inclusive of all values and subranges therebetween. In one embodiment, a 1 mL bolus of a 30 mg IV dose of meloxicam provides an average plasma $C_{max}$ within about 80% to about 125% of the range of from about 4750 ng/mL to about 7250 ng/mL in a patient who is at least 65 year old with mild renal impairment, inclusive of all values and subranges therebetween. In one embodiment, a 1 mL bolus of a 30 mg IV dose of meloxicam provides an average plasma $C_{max}$ within about 80% to about 125% of the range of from about 5000 ng/mL to about 7000 ng/mL in a patient who is at least 65 year old with mild renal impairment, inclusive of all values and subranges therebetween.

In one embodiment, a repeat dose (e.g., administered once daily) of a 1 mL bolus of a 30 mg IV dose of meloxicam provides plasma $C_{max}$ within about 80% to about 125% of the range of from about 10632.5±4729.8 ng/mL in a patient who is at least 65 year old with mild renal impairment, inclusive of all values and subranges therebetween. In one embodiment, a repeat dose of 1 mL of a 30 mg IV dose of meloxicam provides plasma $C_{max}$ within the range of from about 4,722.2 ng/mL to about 19,202.9 ng/mL in a patient who is at least 65 year old with mild renal impairment, inclusive of all values and subranges therebetween. That is, a repeat dose of 30 mg IV dose of meloxicam can provide plasma $C_{max}$ of about 4500 ng/mL, about 4600 ng/mL, about 4700 ng/mL, about 4800 ng/mL, about 4900 ng/mL, about 5000 ng/mL, about 5100 ng/mL, about 5200 ng/mL, about 5300 ng/mL, about 5400 ng/mL, about 5500 ng/mL, about 5600 ng/mL, about 5700 ng/mL, about 5800 ng/mL, about 5900 ng/mL, about 6000 ng/mL, about 6100 ng/mL, about 6200 ng/mL, about 6300 ng/mL, about 6400 ng/mL, about 6500 ng/mL, about 6600 ng/mL, about 6700 ng/mL, about 6800 ng/mL, about 6900 ng/mL, about 7000 ng/mL, about 7100 ng/mL, about 7200 ng/mL, about 7300 ng/mL, about 7400 ng/mL, about 7500 ng/mL, about 7600 ng/mL, about 7700 ng/mL, about 7800 ng/mL, about 7900 ng/mL, about 8000 ng/mL, about 8100 ng/mL, about 8200 ng/mL, about 8300 ng/mL, about 8400 ng/mL, about 8500 ng/mL, about 8600 ng/mL, about 8700 ng/mL, about 8800 ng/mL, about 8900 ng/mL, about 9000 ng/mL, about 9100 ng/mL, about 9200 ng/mL, about 9300 ng/mL, about 9400 ng/mL, about 9500 ng/mL, about 9600 ng/mL, about 9700 ng/mL, about 9800 ng/mL, about 9900 ng/mL, about 10000 ng/mL, about 10100 ng/mL, about 10200 ng/mL, about 10300 ng/mL, about 10400 ng/mL, about 10500 ng/mL, about 10600 ng/mL, about 10700 ng/mL, about 10800 ng/mL, about 10900 ng/mL, about 11000 ng/mL, about 11100 ng/mL, about 11200 ng/mL, about 11300 ng/mL, about 11400 ng/mL, about 11500 ng/mL, about 11600 ng/mL, about 11700 ng/mL, about 11800 ng/mL, about 11900 ng/mL, about 12000 ng/mL, about 12100 ng/mL, about 12200 ng/mL, about 12300 ng/mL, about 12400 ng/mL, about 12500 ng/mL, about 12600 ng/mL, about 12700 ng/mL, about 12800 ng/mL, about 12900 ng/mL, about 13000 ng/mL, about 13100 ng/mL, about 13200 ng/mL, about 13300 ng/mL, about 13400 ng/mL, about 13500 ng/mL, about 13600 ng/mL, about 13700 ng/mL, about 13800 ng/mL, about 13900 ng/mL, about 14000 ng/mL, about 14100 ng/mL, about 14200 ng/mL, about 14300 ng/mL, about 14400 ng/mL, about 14500 ng/mL, about 14600 ng/mL, about 14700 ng/mL, about 14800 ng/mL, about 14900 ng/mL, about 15000 ng/mL, about 15100 ng/mL, about 15200 ng/mL, about 15300 ng/mL, about 15400 ng/mL, about 15500 ng/mL, about 15600 ng/mL, about 15700 ng/mL, about 15800 ng/mL, about 15900 ng/mL, about 16000 ng/mL, about 16100 ng/mL, about 16200 ng/mL, about 16300 ng/mL, about 16400 ng/mL, about 16500 ng/mL, about 16600 ng/mL, about 16700 ng/mL, about 16800 ng/mL, about 16900 ng/mL, about 17000 ng/mL, about 17100 ng/mL, about 17200 ng/mL, about 17300 ng/mL, about 17400 ng/mL, about 17500 ng/mL, about 17600 ng/mL, about 17700 ng/mL, about 17800 ng/mL, about 17900 ng/mL, about 18000 ng/mL, about 18100 ng/mL, about 18200 ng/mL, about 18300 ng/mL, about 18400 ng/mL, about 18500 ng/mL, about 18600 ng/mL, about 18700 ng/mL, about 18800 ng/mL, about 18900 ng/mL, about 19000 ng/mL, about 19100 ng/mL, about 19200 ng/mL, about 19300 ng/mL, about 19400 ng/mL, about 19500 ng/mL, about 19600 ng/mL, about 19700 ng/mL, about 19800 ng/mL, about 19900 ng/mL, or about 12000 ng/mL, or any values or ranges between above values, in a patient who is at least 65 year old with mild renal impairment.

In one embodiment, 1 mL bolus of a 30 mg IV dose of meloxicam provides an average plasma $AUC_{inf}$ within about 80% to about 125% of the range of from about 55,000 ng*hr/mL to about 190,000 ng*hr/mL in a patient who is at least 65 year old with mild renal impairment, inclusive of all values and subranges therebetween. That is, a 1 mL bolus of a 30 mg IV dose of meloxicam can provide an average plasma $AUC_{inf}$ of about 40,000 ng*hr/mL, about 45,000 ng*hr/mL, about 50,000 ng*hr/mL, about 55,000 ng*hr/mL, about 60,000 ng*hr/mL, about 65,000 ng*hr/mL, about 70,000 ng*hr/mL, about 75,000 ng*hr/mL, about 80,000 ng*hr/mL, about 85,000 ng*hr/mL, about 90,000 ng*hr/mL, about 95,000 ng*hr/mL, about 100,000 ng*hr/mL, about 105,000 ng*hr/mL, about 110,000 ng*hr/mL, about 115,000 ng*hr/mL, about 120,000 ng*hr/mL, about 125,000 ng*hr/mL, about 130,000 ng*hr/mL, about 135,000 ng*hr/mL, about 140,000 ng*hr/mL, about 145,000 ng*hr/mL, about 150,000 ng*hr/mL, about 155,000 ng*hr/mL, about 160,000 ng*hr/mL, about 165,000 ng*hr/mL, about 170,000 ng*hr/mL, about 175,000 ng*hr/mL, about 180,000 ng*hr/mL, about 185,000 ng*hr/mL, about 190,000 ng*hr/mL, about 195,000 ng*hr/mL, about 200,000 ng*hr/mL, about 205,000 ng*hr/mL, about 210,000 ng*hr/mL, about 215,000 ng*hr/mL, about 220,000 ng*hr/mL, about 225,000 ng*hr/mL, about 230,000 ng*hr/mL about 235,000 ng*hr/mL, and about 240,000 ng*hr/mL, or any values or ranges between above values, in a patient who is at least 65 year old with mild renal impairment.

In one embodiment, a 1 mL bolus of a 30 mg IV dose of meloxicam provides an average plasma $AUC_{inf}$ within about 80% to about 125% of the range of from about 45,000 ng*hr/mL to about 95,000 ng*hr/mL in a patient who is at least 65 year old with mild renal impairment, inclusive of all values and subranges therebetween. In one embodiment, a 1 mL bolus of a 30 mg IV dose of meloxicam provides an average plasma $AUC_{inf}$ within about 80% to about 125% of the range of from about 71,800±19,600 ng*hr/mL in a patient who is at least 65 year old with mild renal impairment, inclusive of all values and subranges therebetween. In one embodiment, a 1 mL bolus of a 30 mg IV dose of meloxicam provides an average plasma $AUC_{inf}$ within the range of from about 41,760 ng*hr/mL to about 114,250 ng*hr/mL in a patient who is at least 65 year old with mild renal impairment, inclusive of all values and subranges therebetween. In one embodiment, a 1 mL bolus of a 30 mg IV dose of meloxicam provides an average plasma $AUC_{inf}$ within the range of from about 80% to about 125% of about 45,000 ng*hr/mL to about 110,000 ng*hr/mL in a patient who is at least 65 year old with mild renal impairment, inclusive of all values and subranges therebetween. In one embodiment, a 1 mL bolus of a 30 mg IV dose of meloxicam provides an average plasma $AUC_{inf}$ within about 80% to about 125% of the range of from about 45,000 ng*hr/mL to about 100,000 ng*hr/mL in a patient who is at least 65 year old with mild renal impairment, inclusive of all values and subranges therebetween. In one embodiment, a 1 mL bolus of a 30 mg IV dose of meloxicam provides an average plasma $AUC_{inf}$ within about 80% to about 125% of the range of from about 50,000 ng*hr/mL to about 95,000 ng*hr/mL in a patient who is at least 65 year old with mild renal impairment, inclusive of all values and subranges therebetween. In one embodiment, a 1 mL bolus of a 30 mg IV dose of meloxicam provides an average plasma $AUC_{inf}$ within about 80% to about 125% of the range of from about 55,000 ng*hr/mL to about 90,000 ng*hr/mL in a patient who is at least 65 year old with mild renal impairment, inclusive of all values and subranges therebetween.

In one embodiment, a repeat dose (e.g., once daily) of a 1 mL bolus of a 30 mg IV dose of meloxicam provides an average plasma $AUC_{inf}$ within about 80% to about 125% of the range of from about 55,000 ng*hr/mL to about 540,000 ng*hr/mL in a patient who is at least 65 year old with mild renal impairment, inclusive of all values and subranges therebetween. In one embodiment, a repeat dose of a 1 mL bolus of a 30 mg IV dose of meloxicam provides an average plasma $AUC_{inf}$ within about 80% to about 125% of the range of from about 80,000 ng*hr/mL to about 500,000 ng*hr/mL in a patient who is at least 65 year old with mild renal impairment, inclusive of all values and subranges therebetween. In one embodiment, a repeat dose of a 1 mL bolus of a 30 mg IV dose of meloxicam provides an average plasma $AUC_{inf}$ of about within about 80% the range of from to about 125% 100,000 ng*hr/mL to about 450,000 ng*hr/mL in a patient who is at least 65 year old with mild renal impairment, inclusive of all values and subranges therebetween. In one embodiment, a repeat dose of a 1 mL bolus of a 30 mg IV dose of meloxicam provides an average plasma $AUC_{inf}$ within about 80% to about 125% of the range of from about 150,000 ng*hr/mL to about 400,000 ng*hr/mL in a patient who is at least 65 year old with mild renal impairment, inclusive of all values and subranges therebetween. In one embodiment, a repeat dose of a 1 mL bolus of a 30 mg IV dose of meloxicam provides an average plasma $AUC_{inf}$ within about 80% to about 125% of the range of from about 200,000 ng*hr/mL to about 350,000 ng*hr/mL in a patient who is at least 65 year old with mild renal impairment, inclusive of all values and subranges therebetween. In one embodiment, a repeat dose of a 1 mL bolus of a 30 mg IV dose of meloxicam provides an average plasma $AUC_{inf}$ within about 80% to about 125% of the range of from about 250,000 ng*hr/mL to about 325,000 ng*hr/mL in a patient who is at least 65 year old with mild renal impairment, inclusive of all values and subranges therebetween.

In one embodiment, a single 30 mg IV dose of meloxicam provides an average plasma $T_{max}$ of about 0.05 h to about 0.20 h in a patient who is at least 65 year old with mild renal impairment, inclusive of all values and subranges therebetween. That is, a single 30 mg IV injection of meloxicam can provide an average plasma $T_{max}$ of about 0.05 h, about 0.06 h, about 0.07 h, about 0.08 h, about 0.09 h, about 0.10 h, about 0.11 h, about 0.12 h, about 0.13 h, about 0.14 h, about 0.15 h, about 0.16 h, about 0.17 h, about 0.18 h, about 0.19 h, or about 0.20 h, or any values or ranges between above values, in a patient who is at least 65 year old with mild renal impairment.

In one embodiment, 1 mL of a 30 mg IV bolus dose of meloxicam provides an average plasma $T_{max}$ of about 0.06 h to about 0.10 h in a patient who is at least 65 year old with mild renal impairment, inclusive of all values and subranges therebetween. In one embodiment, 1 mL of a 30 mg IV bolus dose of meloxicam provides an average plasma $T_{max}$ of about 0.07 h to about 0.09 h in a patient who is at least 65 year old with mild renal impairment, inclusive of all values and subranges therebetween. In one embodiment, 1 mL of a 30 mg IV bolus dose of meloxicam provides an average plasma $T_{max}$ of about 0.08 h in a patient who is at least 65 year old with mild renal impairment.

An orally administered meloxicam has a prolonged absorption, with plasma $T_{max}$ of about 5-6 hours following administration. The methods as disclosed herein provides significantly faster $T_{max}$, e.g., about 0.06 h to about 0.10 h following administration, which is indicative of rapid onset and fast absorption.

In one embodiment, the method as disclosed herein can provide meloxicam peak analgesic effect within about 30 minutes to about 60 minutes. That is, the administration of 30 mg IV injection of meloxicam can provide peak analgesic effect in about 30 minutes, about 35 minutes, about 40 minutes, about 45 minutes, about 50 minutes, about 55 minutes, or about 60 minutes, or any values or ranges between above values. In one embodiment, the administration of 30 mg/mL IV injection (including a bolus injection) of meloxicam can provide peak analgesic effect in about 40 minutes.

Not only is the meloxicam administration as disclosed herein provide a fast onset of pain relief, it also reaches peak analgesic effect sooner than other known IV NSAIDs (Ketorolac can take 1 to 2 hours for maximum effect) and has a longer therapeutic window of at least about 24 hours (Ketorolac's duration of analgesic effect is 4 to 6 hours). See Ketorolac Tromethamine Injection Prescribing Information.

EXAMPLES

Example 1: Meloxicam 30 mg IV Injection Formulation

IV injection formulation is prepared as ready-to-use formulation containing 30 mg meloxicam, povidone, sodium deoxycholate (deoxycholic acid), sucrose, and water for injection with a total volume of 1 mL in a ready-to-use vial.

Example 2: Predicted Pharmacokinetics (PK) Parameters of Meloxicam Following a 30 mg IV Dose in Subjects with Renal Impairment A population PK analysis of meloxicam was performed based on total population of 316 subjects enrolled in various meloxicam studies to explore sources of variability in drug exposure. The 316 subjects included 75 male (23.7%) and 241 female (76.3%) subjects, mainly of White racial origin (66.1%) and considered non-elderly. The majority of subjects (79.4%) included in the population PK analysis received 30 mg doses of meloxicam. In terms of renal function, 147 (46.5%), 161 (50.9%) and 8 (2.5%) subjects were categorized as normal, mild and moderately impaired based on their baseline eGFR (estimated glomerular filtration rate).

Using the PK dataset obtained from these subjects, the dependencies of renal function on clearance (from central (CL) or peripheral compartments) was calculated. The calculation suggested that the clearance of meloxicam was moderately dependent on renal function (see Table 1). As shown in Table 1, from this model study, patients' clearance of meloxicam decreased with the degree of renal impairment. Thus, it was predicted that patients with renal impairments may require a reduced dose of meloxicam than patients with normal renal function.

The predicted PK parameters of IV dose of meloxicam in Table 1 is different from the PK parameters for Mobic® in patients with mild and moderate renal impairment. See Mobic® Prescribing Information.

TABLE 1

Predicted PK Parameters of meloxicam following a 30 mg dose in subjects with renal impairment

| Typical Patient | Typical Values | | | | |
| --- | --- | --- | --- | --- | --- |
| | eGFR (mL/min) | CL (L/h) | $t_{1/2}$, (h) | $AUC_{0\text{-}inf}$ (ng · h/mL) | $AUC_{0\text{-}inf}$ Ratio (RI/Normal) |
| Normal Renal Function | 120 | 0.485 | 15 | 61856 | NA |
| Overall Population (Median eGFR) | 91 | 0.416 | 17 | 72115 | NA |
| Mild RI | 75 | 0.374 | 19 | 80214 | 1.30 |
| Moderate RI | 45 | 0.282 | 24 | 106383 | 1.72 |
| Severe RI | 22.5 | 0.189 | 36 | 158730 | 2.57 |

Normal renal function (eGFR ≥90 mL/min), Mild RI (eGFR 60-89 mL/min), Moderate RI (eGFR 30-59 mL/min) and Severe RI (eGFR 15-29 mL/min), RI = renal impairment, eGFR = creatinine clearance

Example 3: Study of Pharmacokinetics (PK) and Safety of Meloxicam IV Dose in Subjects with Mildly Impaired Renal Function This study was a single-center, open-label evaluation of the pharmacokinetics and safety, of single doses of meloxicam in elderly subjects with impaired renal function compared with healthy controls. The study enrolled 12 subjects. Eligible subjects were assigned to a study cohort based on their age and renal function. Renal function was assessed using below the equation for estimation of the glomerular filtration rate (GFR).

$$\text{GFR}(\text{mL/min}/1.73 \text{ m}^2) = 175 \times (\text{SCr})^{-1.154} \times (\text{Age})^{-0.203} \times (0.742 \text{ if female}) \times (1.212 \text{ if African American})$$

SCr=serum creatinine measured with a standardized assay.

Enrolled subjects were matched between cohorts according to gender and BMI (±20%). Subjects were assigned to cohorts as follows:

Cohort 1 (n=6; 3 male, 3 female): subjects aged 65 to 80 years with impaired renal function (GFR 60-89 mL/min/1.73 m²)

Cohort 2 (n=6; 3 male, 3 female): subjects aged 18 to 55 years with normal renal function (GFR≥90 mL/min/1.73 m²).

Enrolled subjects returned to the study center on the day before dosing (Day −1). During the treatment visit (Day −1 to Day 3), subjects received a single IV dose 30 mg (25 mg/mL) meloxicam. Whole blood samples were collected for pharmacokinetic (PK) analysis prior to dosing and 5, 10, 20, 30, and 45 minutes, and 1, 2, 4, 6, 12, 18, 24, 36, and 48 hours after dosing.

Safety assessments included monitoring of AEs (adverse events), clinical laboratory tests, vital sign measurements, and ECGs. Upon completion of the treatment visit through Hour 48 (Day 3) assessments, the subjects were discharged from the study center.

Subjects were asked to return to the study center daily for PK sampling at Hour 72 (Day 4), Hour 96 (Day 5), Hour 120 (Day 6), and Hour 144 (Day 7).

Pharmacokinetics

Meloxicam plasma concentrations and PK parameters observed in this study were generally similar between subject cohorts. There was no difference in $T_{max}$ (0.08 hours for all subjects); plasma $C_{max}$ geometric means were 5870 ng/mL for the subjects with mild renal impairment (Cohort 1) and 5580 ng/mL for the healthy control subjects (Cohort 2) where the ratio of the geometric means (RGM; Cohort 1/Cohort 2) and 90% CI (confidence interval) for the RGM was 105% (91% to 121%). A slightly prolonged $t_{1/2}$ was observed in Cohort 1 (mean $t_{1/2}$ was 21.3 h) compared with Cohort 2 (mean $t_{1/2}$ was 17.5 h). plasma $AUC_{0-\infty}$ (area under the concentration-time curve from time 0 to infinity) geometric mean was 69800 hr·ng/mL for Cohort 1 and 65100 hr·ng/mL for Cohort 2 and RGM and 90% CI was 107% (77% to 149%). plasma $AUC_{0-t}$ (area under the concentration-time curve from time 0 to last time point with measurable concentration) results were similar to plasma $AUC_{0-\infty}$. These results indicated that there were no differences between the cohort groups in plasma $C_{max}$ (as defined by 90% CI within the bounds 70%-143%) and $T_{max}$, while the plasma AUC (plasma $AUC_{0-t}$ and plasma $AUC_{0-\infty}$) upper bound exceeded the predefined boundary of 143% (See FIG. 1). However, because of the small deviation outside the defined bounds of the 90% CI, and the low least square geometric mean ratio (107%) between the cohorts, it is reasonable to conclude that there is unlikely to be a meaningful clinical difference between the groups in meloxicam exposure. Although the slightly prolonged $t_{1/2}$ may contribute to the small deviation outside the defined upper bound of the 90% CI for plasma AUCs, the identified difference is expected to be related to the greater variability associated with the small sample size. A summary of PK parameters by cohort is provided in Table 2, with a statistical comparison of some PK parameters in Table 3.

TABLE 2

Summary (Mean ± SD) of PK Parameters

| Parameter | Cohort 1 | | Cohort 2 | |
|---|---|---|---|---|
| | N | Mean ± SD | N | Mean ± SD |
| $C_{max}$, ng/mL | 6 | 5920 ± 842 | 6 | 5620 ± 713 |
| $T_{max}$, h[a] | 6 | 0.08 (0.08-0.08) | 6 | 0.08 (0.08-0.08) |
| $AUC_{0-6}$, h · ng/mL | 6 | 16100 ± 1700 | 6 | 16300 ± 2170 |
| $AUC_{0-12}$, h · ng/mL | 6 | 26000 ± 2690 | 6 | 26400 ± 3920 |
| $AUC_{0-24}$, h · ng/mL | 6 | 40600 ± 4750 | 6 | 41000 ± 8670 |
| $AUC_{0-t}$, h · ng/mL | 6 | 70900 ± 18500 | 6 | 67900 ± 22500 |
| $AUC_{0-\infty}$, h · ng/mL | 6 | 71800 ± 19600 | 6 | 68500 ± 22800 |
| $k_{el}$, 1/h | 6 | 0.0335 ± 0.00606 | 6 | 0.0432 ± 0.0153 |
| t½, h | 6 | 21.3 ± 4.19 | 6 | 17.5 ± 5.16 |
| CL, L/h | 6 | 0.440 ± 0.102 | 6 | 0.488 ± 0.188 |

[a]Median (range).
$AUC_{0-6}$ = area under the concentration-time curve from time 0 to 6 hours after dosing
$AUC_{0-12}$ = area under the concentration-time curve from time 0 to 12 hours after dosing
$AUC_{0-24}$ = area under the concentration-time curve from time 0 to 24 hours after dosing
$AUC_{0-t}$ = area under the concentration-time curve from time 0 to last time point with measurable concentration
$AUC_{0-\infty}$ = area under the concentration-time curve from time 0 to infinity
$k_{el}$ = elimination rate constant
CL = clearance

TABLE 3

Statistical Comparisons of PK Parameters

| Parameter | Least Square Geometric Mean | | Least Square Geometric Mean Ratio (%) | 90% Confidence Interval of |
|---|---|---|---|---|
| | Cohort 1 | Cohort 2 | (Cohort 1/Cohort 2) | the Ratio (%) |
| $C_{max}$, ng/mL | 5870 | 5580 | 105 | (91.02, 121.46) |
| $AUC_{0-t}$, h · ng/mL | 69100 | 64500 | 107 | (77.50, 147.83) |
| $AUC_{0-\infty}$, h · ng/mL | 69800 | 65100 | 107 | (77.36, 148.83) |

Safety

All subjects had a single IV dose of 30 mg meloxicam. Doses of study medication were well tolerated with no incidence of death, SAEs (severe adverse events), or discontinuations due to an AE during the study. There was a low incidence of adverse events (33.3% of subjects with any event) with no subject experiencing more than one event. AEs were generally mild or moderate in intensity, and consistent with the AE profile of meloxicam in previous studies. There were no clinically significant vital sign or ECG (electrocardiogram) findings, and only one clinically significant laboratory assessment change. Administration of 30 mg meloxicam as an IV infusion over 17-20 seconds was not associated with any infusion, or infusion site, reactions.

Administration of meloxicam at the 30 mg dose level was safe and well tolerated in healthy, as well as subjects with mild renal impairment. The safety profile of meloxicam was comparable between subject cohorts. The study identified no difference between cohorts in the achieved plasma $C_{max}$. Further, it is reasonable to conclude from this study that there was not a meaningful clinical difference between the cohorts in meloxicam exposure. Thus, dose modification for elderly subject with mild renal impairment is not necessary.

Example 4: Treatment of Pain Following Surgery with Repeat Dose of 30 mg Meloxicam IV Infusion in Elderly Patients with Impaired Renal Function This was a multi-center, randomized, double-blind, placebo-controlled study in male and female subjects, age 18-80 years scheduled to undergo major elective surgery with an inpatient hospital stay expected to exceed 24 hours. Study participation included a screening visit with written informed consent, an inpatient visit including surgery and study treatment, and two follow-up visits after discharge (one in office and one by phone). Subjects underwent major surgeries according to the standard practice of the institution. Following surgery, eligible subjects were stratified, randomized (3:1), and administered IV meloxicam 30 mg or placebo via IV over 15-30 seconds every 24 hours for up to 7 doses. Subjects could continue to receive opioid analgesia according to the practice of the investigator to treat uncontrolled pain symptoms; additional NSAIDs were prohibited during inpatient treatment. Opioid use was measured throughout the postoperative inpatient phase and converted to the total IV morphine equivalent dose for summary. Safety assessments included clinical laboratory tests, vital signs, ECGs, surgical wound assessment, total opioid use, and monitoring of adverse events (AEs) and serious AEs (SAES). The primary objective of the study was to evaluate the safety of IV meloxicam 30 mg compared with placebo according to the collected safety assessments.

Figure 2:
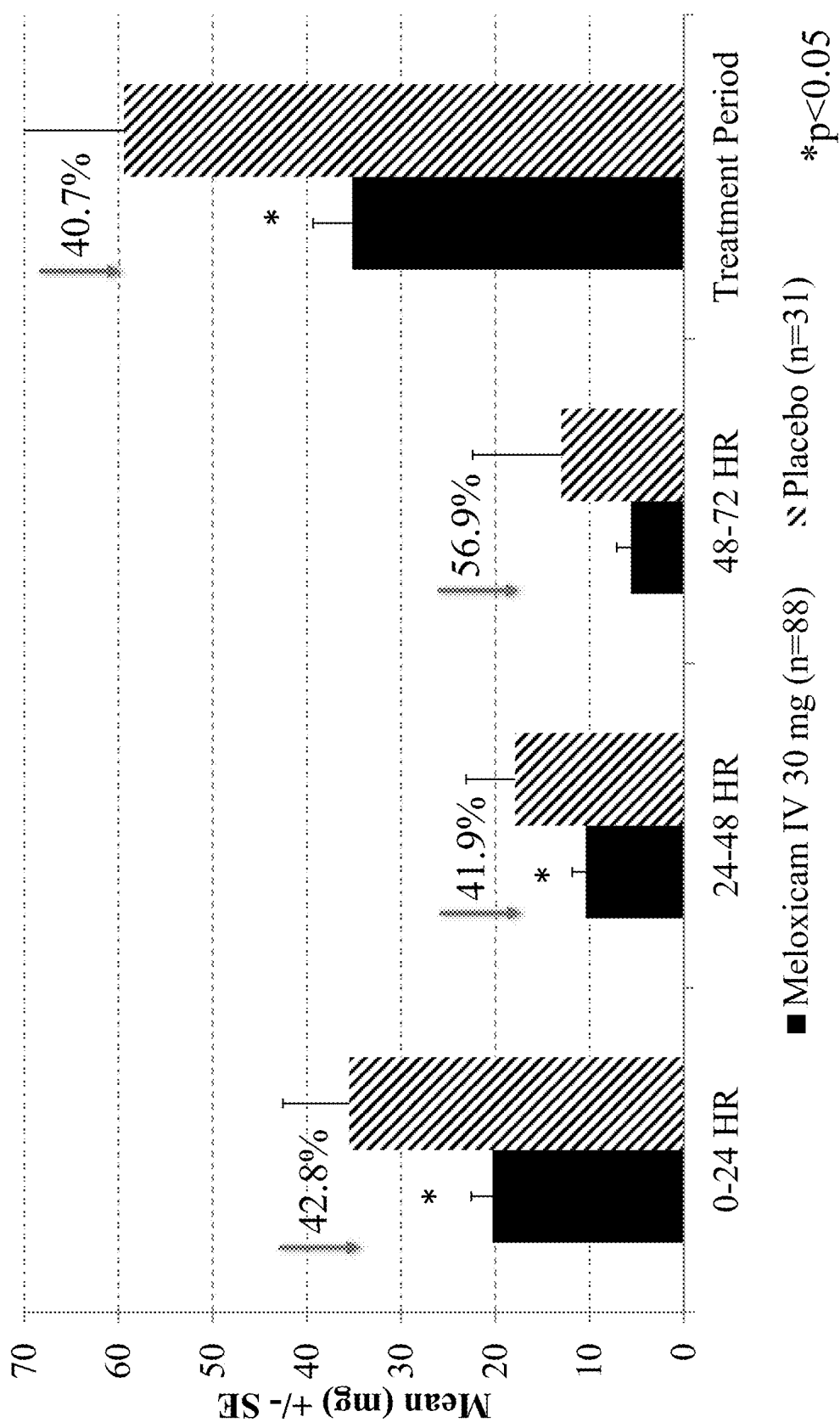
FIG. 2 is a summary of postoperative opioid analgesic use in subjects studied in Example 4.

The study randomized and treated 119 subjects of advanced age with impaired renal function; 88 randomized to IV meloxicam 30 mg, and 31 to placebo. Subjects ranged in age from 66 to 80 years, with a mean age of 70.5 years. The majority of subjects were female (57.1%) and white (95.0%), with demographics similar between the treatment groups. Surgery categories included orthopedic, abdominal/pelvic, and spinal, with an overall mean surgery duration of 1.5 hours, and a mean time to first dose of study drug occurring 1.9 hours following the end of surgery. The majority of subjects (>80%) received 2 or 3 doses of study drug during their inpatient stay. IV meloxicam 30 mg was well tolerated with no deaths or discontinuations due to an AE, and a low incidence of SAEs (2.3% of IV meloxicam vs. 12.9% of placebo). AEs were generally mild or moderate in intensity, and similar between treatments. The most common treatment-emergent AEs included nausea, constipation, vomiting, anemia, pruritus, hypotension, insomnia, and gamma-glutamyl transferase increased. Administration of IV meloxicam was well tolerated with no injection site AEs. Events related to bleeding, cardiovascular, hepatic, renal, thrombotic, and wound healing complications were infrequent and generally similar between treatment groups. There was a low incidence of clinically meaningful changes in laboratory, vital sign, and ECG assessments during the study, with findings similar between treatments. Investigator assessments of surgical wound healing status were favorable and consistent between treatments. Mean opioid consumption was numerically lower in the IV meloxicam 30 mg group compared with placebo at all evaluated intervals, reaching statistical significance (p<0.05) in the Hour 0-24 and Hour 24-48 intervals with 42.8% and 41.9% reductions in opioid use respectively (FIG. 2).

IV meloxicam 30 mg daily was well tolerated in subjects of advanced age with impaired renal function compared with placebo, with no discontinuations due to an AE, and a low incidence of SAEs. AEs were generally mild or moderate in intensity, and similar in incidence between treatment groups. Statistically significant reductions in opioid use, up to 42.8%, were observed during treatment with IV meloxicam compared with placebo. This study supports the safety and tolerability of IV meloxicam 30 mg administered once daily for up to 7 days following major surgery in subjects aged >65 years with impaired renal function.

The disclosures of all publications, patents, patent applications and published patent applications referred to herein by an identifying citation are hereby incorporated herein by reference in their entirety.

In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A method of treating pain, comprising administering to a patient in need thereof meloxicam intravenously at a dose of about 30 mg, wherein the patient is at least 65 years old and has mild renal impairment;
    wherein administration of meloxicam at the dose of about 30 mg is safe and well tolerated with no clinically meaningful differences between the patient and subjects aged 18 to 55 years with normal renal function (GFR>90 mL/min/1.73 m$^2$), and the meloxicam is present as meloxicam nanocrystals.

2. The method of claim 1, wherein the dose of meloxicam is administered to the patient in a bolus dose.

3. The method of claim 1, wherein the dose of meloxicam is administered to the patient over the course of about 1 to about 60 seconds.

4. The method of claim 3, wherein the dose of meloxicam is administered to the patient over the course of about 15 to about 30 seconds.

5. The method of claim 1, wherein the meloxicam is present in a volume of from about 0.5 mL to about 4 mL.

6. The method of claim 5, wherein the meloxicam is present in a volume of about 1 mL.

7. The methods of claim 1, wherein the pain is post-surgical pain.

8. The method of claim 1, wherein the dose of meloxicam is administered after the patient has undergone a surgical procedure.

9. The method of claim 8, wherein the surgical procedure is an open surgical procedure.

10. The method of claim 8, wherein the surgical procedure is a laparoscopic surgical procedure.

11. The method of claim 8, wherein the surgical procedure was performed on hard tissue.

12. The method of claim 8, wherein the surgical procedure was performed on soft tissue.

13. The method of claim 1, wherein the pain is moderate to severe pain.

14. The method of claim 1, wherein the pain is mild to moderate pain.

15. The method of claim 1, further comprising administering meloxicam to the patient about every 16 hours to about every 26 hours after administering to the patient meloxicam intravenously at a dose of about 30 mg, and until the patient is no longer in need thereof.

16. The method of claim 1, wherein meloxicam is administered to the patient about 18 hours to about every 24 hours after administering to the patient meloxicam intravenously at a dose of about 30 mg, and until the patient is no longer in need thereof.

* * * * *